United States Patent [19]

Frank et al.

[11] Patent Number: 5,565,583
[45] Date of Patent: Oct. 15, 1996

[54] PREPARATION OF 2-SUBSTITUTED BUT-2-ENE-1, 4-DIAL-4-ACETALS AND NOVEL HEMIACETALS OF GLYOXAL MONOACETALS

[75] Inventors: Jürgen Frank, Ludwigshafen; Johann-Peter Melder, Mannheim; Franz Merger, Frankenthal; Tom Witzel, Ludwigshafen, all of Germany

[73] Assignee: BASF Aktiengesellschaft, Ludwigshafen, Germany

[21] Appl. No.: 465,532

[22] Filed: Jun. 5, 1995

Related U.S. Application Data

[62] Division of Ser. No. 314,955, Sep. 29, 1994.

[30] Foreign Application Priority Data

Sep. 30, 1993 [DE] Germany ............... 43 33 239.0

[51] Int. Cl.⁶ .................................. C07D 319/06
[52] U.S. Cl. ............................ 549/374; 549/375
[58] Field of Search .................................. 549/374

[56] References Cited

U.S. PATENT DOCUMENTS

| 4,835,320 | 5/1989 | Blanc et al. | 568/465 |
| 5,162,552 | 11/1992 | Merger et al. | 549/375 |

*Primary Examiner*—Nicky Chan
*Attorney, Agent, or Firm*—Keil & Weinkauf

[57] ABSTRACT

Hemiacetals of glyoxal monoacetals are useful as intermediates to prepare 2-substituted but-2-en-1,4-dial-4-acetals of the general formula I;

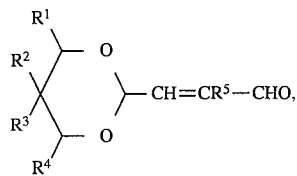

1 Claim, No Drawings

PREPARATION OF 2-SUBSTITUTED BUT-2-ENE-1, 4-DIAL-4-ACETALS AND NOVEL HEMIACETALS OF GLYOXAL MONOACETALS

This is a division of application Ser. No. 08/314,955, filed Sep. 29, 1964.

The present invention relates to a process for the preparation of but-2-ene-1,4-dial-4-acetals of the general formula I

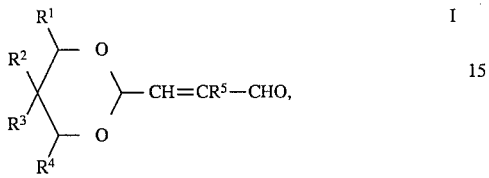

in which the substituents $R^1$ to $R^4$ stand for hydrogen or $c_1$–$C_6$ aliphatic radicals, and $R^2$ and $R^3$ or $R^1$ and $R^2$ are in each case common members of an aliphatic 4-membered to 7-membered ring, which can contain a hetero atom, and $R^5$ denotes an alkyl, alkenyl, or alkynyl radical having from 1 to 12 C atoms, which can be substituted by cycloaliphatic, aromatic or heterocyclic radicals or by hydroxy, ether, thioether, acyl, alkylamino, carboxy, or carbalkoxy groups, an optionally substituted aryl radical or an alkoxy, alkylthio, or acyloxy group.

Furthermore, the invention relates to novel hemiacetals of glyoxal monoacetals.

EP-A 249,530 teaches the preparation of glyoxal monoacetals from glyoxal and alcohols in the presence of catalytic amounts of acid and of a molar excess of alcohol. EP-A 316,672 describes the preparation of the glyoxal monoacetals by reaction of glyoxal with 1,3-propanediol derivatives in the presence of water and an acid at temperatures of up to 150° C. According to the teaching of these two references the products are isolated predominantly by distillation. During such a process the formation of high-boiling oligomers leads to losses of yield, since these only partly remonomerize thermally. In order to achieve useful total yields of glyoxal monoacetals on an industrial scale it is in addition necessary to recycle to the reaction all of the by-products and starting products isolated by distillation, since this is the only way of carrying out the overall process in an economical manner.

EP-A 246,646 describes the preparation of 4-acetals of but-2-en-1,4-dials from glyoxal monoacetals and aldehydes at from 20° to 150° C. In a preferred mode of operation this reaction is carried out in the presence of from 2 to 100 mol%, based on the glyoxal monoacetal, of a catalyst comprising a secondary amine and an acid. Such a large amount of catalyst demands, for economical reasons, separation of the catalyst and recycling following the reaction.

It was thus the object of the invention to provide an industrially simple process for the preparation of but-2-ene-1,4-dial-4-acetals from glyoxal, which avoids the drawbacks of the prior process steps described above.

Accordingly, we have found the process defined above, wherein a glyoxal is caused to react with a 1,3-propanediol of the general formula II

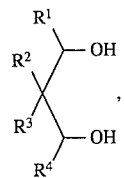

in aqueous solution in the presence of an acid to form a monoacetal of the general formula III

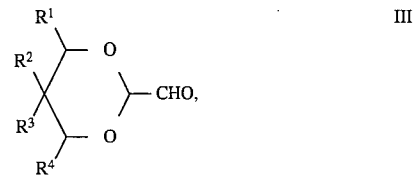

is neutralized, and if necessary the components more readily volatile than the monoacetal III are distilled off, b) the monoacetal III obtained is caused to react with an aldehyde $R^5CH_2$—CHO in the presence of from 0.01 to 10 mol%, based on glyoxal, of a catalyst mixture of a secondary amine and an acid to form an aldol of the general formula IV

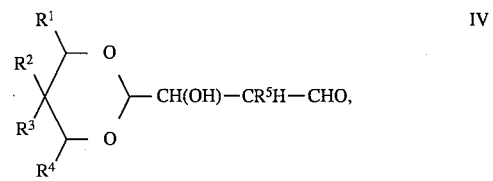

the components which are more volatile than the aldol IV being distilled off if necessary, and c) the aldol IV is dehydrated in the presence of a water-eliminating agent to form the product I.

Furthermore, we have found novel hemiacetals of glyoxal monoacetals.

Process step a)

Glyoxal is preferably used in the form of an aqueous solution, it being advantageous to use the usual industrial aqueous solutions having a glyoxal content of from 20 to 60 wt%, preferably from 30 to 50 wt%.

The 1,3-propanediols of the general formula II carry as radicals $R^1$ to $R^4$ hydrogen atoms or aliphatic radicals having from 1 to 6 carbon atoms. These radicals can be straight-chained, branch-chained or cycloaliphatic radicals, such as alkyl groups having preferably from 1 to 4 carbon atoms, or cycloalkyl groups having from 4 to 6 carbon atoms. The radicals $R^1$ and $R^2$ or $R^2$ and $R^3$ can also in each case be common members of an aliphatic 4-membered to 7-membered, preferably 5-membered to 6-membered, ring, which can contain a hetero atom, in each case one oxygen or nitrogen atom. For example, there may be mentioned the following aliphatic radicals: methyl, ethyl, propyl, isopropyl, butyl, and cyclohexyl. Suitable aromatic radicals are eg phenyl radicals. Aliphatic 4-membered to 7-membered rings, which can also contain a hetero atom, are eg cyclopentane, cyclohexane or tetrahydropyran. Specifically, there may be mentioned the following 1,3-propanediols: 2,2-dimethyl-1,3-propanediol, 2-ethyl-2-methyl-1,3-propanediol, 2-butyl-2-ethyl-1,3-propanediol, 1-isopropyl-2,2-dimethyl-1,3-propanediol, and 1-propyl-2-ethyl-1,3-propanediol.

For each mole of glyoxal there are usually employed from 0.1 to 5 mol, preferably from 0.5 to 2 mol of the 1,3-propanediol of the formula II.

The reaction of the glyoxal with the 1,3-propanediol is carried out in the presence of catalytic amounts of acid. Suitable acids for this purpose are eg mineral acids such as sulfuric acid, sulfonic acids such as methanesulfonic acid, p-toluenesulfonic acid, carboxylic acids such as trichloroacetic acid and oxalic acid, and also acid ion exchangers. Generally speaking, the acids are used in amounts of from 0.01 to 0.25 mol per mole of glyoxal.

In a preferred embodiment of the process of the invention the reaction is carried out in the presence of a solvent capable of forming two phases with the aqueous starting mixture. Suitable solvents are eg aliphatic, cycloaliphatic, or aromatic hydrocarbons, which can contain eg halogen atoms, hydroxyl groups, and/or alkoxy groups and have two to fifteen carbon atoms. Examples thereof are aliphatic and cycloaliphatic hydrocarbons such as n-hexane, isohexane, isomeric heptanes, octanes, cyclohexanes, haloalkanes such as 1,2-dichloroethane, 1,2-dichloropropane, trichloromethane, tetrachloromethane, 1,1,1- and 1,1,2-trichloroethanes, 1,1,2-trichloroethene, alcohols such as butanols, pentanols, hexanols, ethylhexanol, nonanols, decanols and undecanols, or optionally substituted aromatic hydrocarbons, such as benzene, toluene, xylene, ethylbenzene, isopropylbenzene, durene, tetraline, chlorobenzene, 1,2-dichlorobenzene, or anisol. These solvents, which can also be used in the form of a mixture, are added in amounts of eg from 100 to 2000 mL, preferably from 150 to 1000 mL per mole of diol used. Particularly advantageous results are obtained when the solvents used are mixtures of alkanols such as butanol, pentanol or hexanol on the one hand and aromatic hydrocarbons such as benzene, toluene or xylene on the other hand. The reaction can be carried out under standard pressure, but also under reduced or elevated pressure. Preferably, the pressure of reaction is from 1 to 5 bar.

The temperature of reaction is generally from 20° to 150° C. The process can be carried out batchwise or continuously. The residence time is generally from 1 to 10 h.

On completion of the reaction, the reaction solution is neutralized by the addition of a base such as eg sodium carbonate, sodium hydrogen carbonate, and sodium hydroxide. Alternatively, ammonia, primary amines, secondary amines such as dimethylamine and diethylamine as well as tertiary amines such as triethylamine are suitable neutralizing agents.

If the reaction is carried out in a two-phase solvent mixture, the organic phase containing the product can be separated and also neutralized. Advantageously, the aqueous phase is extracted a number of times with one of the above solvents, eg butanol. These extracts are then combined with the organic phase.

Prior to further reaction thereof, the solutions thus obtained can be concentrated by distilling off the components which are more volatile than the monoacetal III. It is particularly preferred either that there remains in the solution a monoalcohol already used as solvent or that such a monoalcohol is added. As a result, the glyoxal monoacetal is converted to a hemiacetal and is thus protected from oligomerization.

Process step b)

The monoacetals III prepared according to process step a) are caused to react with an aldehyde $R^5CH_2$—CHO. The radical $R^5$ stands for an alkyl, alkenyl, or alkynyl radical having from 1 to 12 C atoms, which can be substituted by cycloaliphatic, aromatic, or heterocyclic radicals or by hydroxy, ether, thioether, acyl, alkylamino, carboxy, or carbalkoxy groups, or denotes an optionally substituted aryl radical or an alkoxy, alkylthio, or acyloxy group. $R^5$ is preferably ethyl, propyl and butyl. Suitable aldehydes are consequently compounds such as propanal, butanal, pentanal, isopentanal, hexanal, isohexanal, decanal and undecanal.

As catalyst system there is used a mixture of a secondary amine and an acid. Suitable acids are preferably carboxylic acids having from 1 to 10 carbon atoms, eg acetic acid, propionic acid, butanoic acid, pentanoic acid, hexanoic acid, and 2-ethylhexanoic acid. Similarly, dicarboxylic acids such as oxalic acid or succinic acid can be used. Examples of the amine component are dialkylamines such as dimethylamine, diethylamine, diisopropylamine, di-n-butylamine, methylethylamine, methylbutylamine, and also hydroxyalkylamines such as diethanolamine, methyl-ethanolamine, or cyclic amines, which can carry further hetero atoms, such as pyrrolidine, piperidine, and morpholine. The catalyst systems are used in amounts of from 0.01 to 10 mol%, based on glyoxal, preferably from 0.1 to 8 mol%. The ratio of amines to acid need not be exactly equimolar. On the contrary, it may be advantageous to operate with a slight excess of acid. It has been found to be advantageous to start with the monoacetal 1III from process step a), and to add the catalyst system thereto. The temperature of reaction during this aldol reaction is generally from 20° to 90° C., preferably from 30° to 80° C.

The reaction time is usually from 15 to 240 minutes.

The reaction solutions thus obtained are concentrated prior to further reaction preferably by distilling off the components which are more volatile than the aldol IV.

Process step c)

For the preparation of the end products I, the aldols IV can be caused to react with a water-eliminating agent, preferably without intermediate isolation, in a manner known per se. These agents are preferably acids, eg mineral acids such as sulfuric acid and phosphoric acid, sulfonic acids such as p-toluenesulfonic acid and methenesulfonic acid, but they may also be acid ion exchangers, anhydrides such as acetic anhydride, phthalic anhydride, and maleic anhydride, of which acetic anhydride is preferred, as well as ketenes.

The process is carried out preferably by adding acetic anhydride to the reaction mixture obtained in accordance with the invention in amounts of from 1 to 5 mol per mole of aldol, and optionally small amounts of a catalyst such as sodium acetate or 4-dimethylamino-pyridine are added, and the mixture is then heated to the boil for a further 1 to 12 h and preferably 2 to 6 h under reflux.

The end products I can be isolated from the reaction solutions by methods known per se, preferably by distillation.

The process of the invention provides a simple method of industrial preparation of the end products I from glyoxal. It is a noteworthy fact that the monoacetals prepared in the process step a) can be caused to react, without isolation by distillation, with an aldehyde to produce the aldols IV, without the by-products obtained in the solution having any adverse effect. Furthermore, it is possible to use such small quantities of catalyst in the process step b) that purification of the catalyst and recycling are not necessary.

The end products are valuable intermediates for the preparation of terpenes and terpene-like compounds having biological and pharmacological activity.

The invention also relates to novel hemiacetals of glyoxal monoacetals V

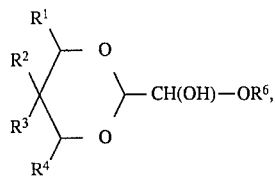

in which R⁶ stands for a straight-chained or branched-chained C₁–C₂ alkyl radical, a C₆–C₂ aryl radical or a C₇–C₂₀ aralkyl radical.

Specifically, the radical R⁶ preferably stands for alkyl radicals such as methyl, ethyl, propyl, butyl, for aryl radicals such as phenyl or for aralkyl radicals such as benzyl.

These products V can be obtained by working up the effluent from process step a) after the addition of a monoalcohol R⁶—OH by distillation. The hemiacetals V can be used in reactions typical for the free aldehyde, for example process step b), instead of the aldehyde. As opposed to the aldehydes they have the advantage that they can be stored without any problem and without any tendency to oligomerization.

EXAMPLES

Example 1

Preparation of 2-methylbut-2-ene-1,4-diol-4-neopentylglycol acetal

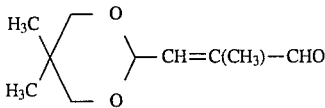

Process stage a)

A mixture of 234 kg (2250 mol) of 2,2-dimethylpropane-1,3-diol, 326 kg (2250 mol) of 40% strength glyoxal in water, 167 kg. of 1-butanol and 900 L of toluene were admixed with 22.5 kg of 50% strength sulfuric acid, and heated for 2 h at 140° C. under an autogenous pressure of from 2.5 to 3 bar. Following cooling to room temperature, the aqueous phase was separated and extracted a number of times with 1-butanol. The butanol extracts were combined with the organic phase, neutralized with a solution of 5 kg of sodium carbonate in 30 kg of water, and separated from the aqueous phase. From the organic phase there was distilled off toluene completely and 1-butanol to a degree of ca 50%, in vacuo.

Process stage b)

The residues from process stage a) were admixed with 175 kg (3020 mol) of propionaldehyde, and 17.5 kg of catalyst solution consisting of 3.1 kg (51 mol) of acetic acid, 5.70 kg (51 mol) of 40% strength dimethylamine and 8.7 kg of water, were added at from 60° to 80° C. Following a reaction time of 30 min at 85° C. there were distilled off in vacuo all components which were more volatile than the aldol product.

Process stage c)

The residues from process stage b) were admixed at 110° C. with 275 kg (2700 mol) of acetic anhydride, and heated for 3 h at 140° C. Following destillation there were isolated 227.7 kg of 2-methylbut-2-ene-1,4-dial-4-neopentylglycol acetal, which is equivalent to a yield of 55%, based on glyoxal.

Example 2

Preparation of 2-(1-hydroxy-2-oxahexyl)-5,5-dimethyl-1,3-dioxane

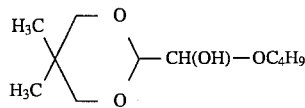

4800 g of the distillation residues of the process stage a) from Example 1 were distilled through a packed column. At a pressure of from 1 to 2 mbar there were isolated, at from 46° to 50° C., 3400 g of 2-(1-hydroxy-2-oxahexyl)-5,5-dimethyl-1,3-dioxane in the form of a colorless oil. The yield was 70%, based on the residues from process stage a).

¹H-NMR (CDCl₃): 0.73 (s, CH₃), 0.9 (m, CH₃), 1.2 (s, CH₃), 1.38 (m, CH₂), 1.6 (m, CH₂), 3,5 (m, CH), 3.55 (m, CH₂), 3.65 (m, CH₂), 3.85 CH), 4.60 ppm (br s, OH).

C-NMR (CDCl₃): 13.9 (1C, CH₃), 19.2 ((1C, CH₂), 21.7 (1C, CH₃), 22.9 (1C, CH₃), 30.4 (1C.), 34.8 (1C., CH₂), 67.9 (1C, CH₂), 76.8 (2C, CH₂), 95.7 (1C, CH), 100.2 ppm (1C, CH).

We claim:

1. A hemiacetal of the formula V

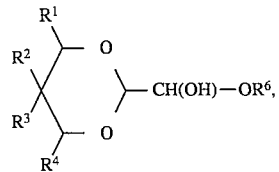

in which R¹ to R⁴ stand for hydrogen or C₁–C₆-aliphatic radicals, and R₆ stands for a straight-chained or branched-chained C₁–C₁₂ alkyl radical, a C₆–C₁₂ aryl radical or a C₇–C₂₀ aralkyl radical.

* * * * *

UNITED STATES PATENT AND TRADEMARK OFFICE
CERTIFICATE OF CORRECTION

PATENT NO.: 5,565,583

DATED: October 15, 1996

INVENTOR(S): FRANK et al.

It is certified that error appears in the above-identified patent and that said Letters Patent is hereby corrected as shown below:

Column 6, claim 1, line 51, "$R_6$" should be --$R^6$--.

Signed and Sealed this

Seventeenth Day of December, 1996

Attest:

BRUCE LEHMAN

*Attesting Officer*   *Commissioner of Patents and Trademarks*